(12) United States Patent
Cartt (10) Patent No.: US 7,608,616 B1
(45) Date of Patent: Oct. 27, 2009

(54) METHODS FOR REDUCING THE RISK OF AN ADVERSE DRUG INTERACTION IN A PATIENT SUFFERING FROM INSOMNIA

(75) Inventor: Steve Cartt, Union City, CA (US)

(73) Assignee: Questcor Pharmaceuticals, Inc., Union City, CA (US)

( * ) Notice: Subject to any disclaimer, the term of this patent is extended or adjusted under 35 U.S.C. 154(b) by 0 days.

(21) Appl. No.: 12/132,575

(22) Filed: Jun. 3, 2008

(51) Int. Cl.
*A61K 31/55* (2006.01)
*A01N 43/62* (2006.01)
*A61K 31/135* (2006.01)
*A01N 33/02* (2006.01)
*A61K 31/12* (2006.01)
*A01N 33/18* (2006.01)
*A01N 33/24* (2006.01)

(52) U.S. Cl. .................. 514/221; 514/649; 514/676

(58) Field of Classification Search .................. 514/221, 514/649, 676
See application file for complete search history.

(56) References Cited

U.S. PATENT DOCUMENTS 6,344,487 B1  2/2002  Kavey

OTHER PUBLICATIONS

Thase ME. "Treatment Issues Related to Sleep and Depression". J Clin Psychiatry, 2000; 61[Suppl 11]:46-50.*
Kales A. "Quazepam: Hypnotic Efficacy and Side Effects". Pharmacotherapy, 1990; 10(1):1-12.*
Reid et al. "Insomnia in HIV Infection: A Systematic Review of Prevalence, Correlates, and Management". Psychosomatic Medicine, 2005; 67:260-269.*
Gallego et al. "Abnormalities in Sleep Architecture in Patients Receiving Efavirenz". Retrovir Oppor Infect 10th 2002 Boston Mass. Feb. 10-14, 2003; 10: Abstract No. 716.*
Nakao et al. "Major Depression and Somatic Symptoms in a Mind/Body Medicine Clinic". Psychopathology; Sep./Oct. 2001; 34(5):230-235.*
Akhondzadeh et al. "Double-Blind Comparison of Fluoxetine and Nortriptyline in the Treatment of Moderate to Severe Major Depression". Journal of Clinical Pharmacy and Therapeutics. 2003; 28:379-384.*
Bupropion Information from Wikipedia Revision as of 3:32, Jun. 3, 2007; http://en.wikipedia.org/wiki/Bupropion.
Turpeinen, M. et al., "Cytochrome P450 (CYP) inhibition screening: Comparison of three tests," Eur. J. Pharmaceutical Sciences 29:130-138 (2006).
Walsky, W.L. et al., "Evaluation of 227 Drugs for In Vitro Inhibition of Cytochrome P450 2B6," J. Clin. Pharmacol. 46:1426-1438 (2006).
Wellbutrin XL Medication Guide, Aug. 2007 manufactured by Biovail Corporation for GlaxoSmithKline.
Clifford, D.B. et al., "Impact of Efavirenz on Neuropsychological Performance and Symptoms in HIV-Infected Individuals," Ann. Intern. Med. 143:714-721 (2006).
Gallego, L. et al., "Analyzing Sleep Abnormalities in HIV-Infected Patients Treated with Efavirenz," CID 38:430-432 (2004).
"Most Effective Initial Therapy For HIV-1 Infection Identified," Science Daily, http://www.sciencedaily.com/releases/2008/05/08051417814.htm, (2008).
Riddler, S.A. et al., "Class-Sparing Regiments for Initial Treatment of HIV-1 Infection," N. Engl. J. Med. 358(20):2095-2106 (2008).

* cited by examiner

*Primary Examiner*—Ardin Marschel
*Assistant Examiner*—Leslie A Royds
(74) *Attorney, Agent, or Firm*—Wilson Sonsini Goodrich & Rosati (57) ABSTRACT

Disclosed herein is a method for treating a patient with Quazepam that reduces the risk of an adverse interaction between the Quazepam and drug that is a substrate of the cytochrome P450 enzyme isoform 2B6 (CYP2B6 substrate drug), e.g., Bupropion. The method includes determining if the patient to be treated with Quazepam is being treated with a CYP2B6 substrate drug, and prescribing or treating the patient with Quazepam based on the determination.

2 Claims, 4 Drawing Sheets

NADPH-Dependency of Time-Dependent Inhibition of CYP2B6-Catalyzed Bupropion
Hydroxylation by Quazepam in Human Liver Microsomes

METHODS FOR REDUCING THE RISK OF AN ADVERSE DRUG INTERACTION IN A PATIENT SUFFERING FROM INSOMNIA

BACKGROUND

Both insomnia and mood disorder conditions are debilitating health conditions that are widespread and can be extremely costly to society. Patients suffering from insomnia may also suffer from a mood disorder (e.g. depression). One of the common side effects of some antidepressants can be insomnia. In some cases patients suffering from insomnia or depression may require treatment with both a drug such as Quazepam (e.g., sold under the tradename Doral®) and a drug such as Bupropion (e.g., sold under the tradename Wellbutrin®).

SUMMARY OF THE INVENTION

Described herein are methods for reducing the risk of an adverse drug interaction during treatment of a patient in need of the sleep drug Quazepam, e.g., a patient suffering from insomnia, by determining whether the patient is being treated with a drug that is a substrate of the cytochrome P450 enzyme isoform 2B6, which is the primary metabolizing enzyme for a number of drugs, e.g., Bupropion and Efavirenz.

Accordingly, provided herein is a method for reducing the risk of an adverse drug interaction in a patient, comprising determining if a patient identified as suffering from insomnia is being treated with a drug that is a substrate of the CYP2B6 enzyme, and prescribing or administering to the patient a therapeutically effective amount of Quazepam if and only if the patient is not being treated with the drug that is a substrate of the CYP2B6 enzyme. In some embodiments, the patient identified as suffering from insomnia also suffers from depression. In some embodiments, where the patient also suffers from depression, the method further comprises prescribing or administering to the patient an antidepressant drug other than Bupropion. In some embodiments, the drug that is the substrate of the CYP2B6 enzyme is Bupropion or Efavirenz.

In a related aspect provided herein is a method for reducing the risk of an adverse drug interaction in a patient suffering from insomnia, comprising:

determining if a patient identified as suffering from insomnia is being treated with a drug that is a substrate of the CYP2B6 enzyme to treat a second condition, and (i) if the patient is being treated with the drug that is a substrate of the CYP2B6 enzyme:
  (a) prescribing or administering a therapeutically effective amount of Quazepam to treat the insomnia, and monitoring the patient for an adverse side effect associated with Quazepam or the drug that is a substrate of the CYP2B6 enzyme; or
  (b) stopping treatment with the drug that is a substrate of the CYP2B6 enzyme, and prescribing or administering a therapeutically effective amount of Quazepam to treat the insomnia.

However, if the patient suffering from insomnia is not being treated with the drug that is a substrate of the CYP2B6 enzyme, the patient is prescribed or administered a therapeutically effective amount of Quazepam to treat the insomnia.

In some embodiments, where the patient is being treated with the drug that is a substrate of the CYP2B6 enzyme, the patient is prescribed or administered a therapeutically effective amount of Quazepam to treat the insomnia, and monitored for an adverse side effect associated with Quazepam or the drug that is a substrate of the CYP2B6 enzyme. In some embodiments, the method includes, in addition to monitoring, reducing the dose of the drug that is a substrate of the CYP2B6 enzyme.

In some embodiments, where the patient is being treated with the drug that is a substrate of the CYP2B6 enzyme, treatment with the drug that is a substrate of the CYP2B6 enzyme is stopped, and the patient is prescribed or administered a therapeutically effective amount of Quazepam to treat the insomnia. In some embodiments, after stopping treatment of the patient with the drug that is a substrate of the CYP2B6, the patient is prescribed or administered a drug that is not a substrate of the CYP2B6 enzyme to treat the second condition.

In some embodiments, where the patient is not being treated with the drug that is a substrate of the CYP2B6 enzyme, the patient is prescribed or administered a therapeutically effective amount of Quazepam to treat the insomnia.

In some embodiments, the drug that is the substrate of the CYP2B6 enzyme is Bupropion or Efavirenz.

In some embodiments, the second condition from which the patient is suffering is depression. In some embodiments, where the patient is also suffering from depression, the patient is prescribed or administered a therapeutically effective amount of an antidepressant drug other than Bupropion. In some embodiments, the antidepressant drug other than Bupropion is not a substrate of the CYP2B6 enzyme.

In a further aspect provided herein is a method for reducing the risk of an adverse drug interaction in a patient being treated with Quazepam, comprising:

determining if the patient is in need of treatment for depression, and, if so, prescribing or administering to the patient a therapeutically effective amount of a drug other than Bupropion. In some embodiments, the drug other than Bupropion is not a substrate of the CYP2B6 enzyme. In other embodiments, the drug other than Bupropion is a substrate of the CYP2B6 enzyme.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless defined otherwise, all technical and scientific terms used herein have the same meaning as is commonly understood by one of skill in the art to which the claimed subject matter belongs.

As used herein, the term "adverse interaction" refers to the co-occurrence in a patient of two or more therapeutic compounds or the metabolites thereof, wherein, for any of the therapeutic compounds, the pharmacokinetic profile is altered, the therapeutic efficacy is reduced, toxicity is increased, or side effects are increased as compared to those observed in a patient in which only one of the therapeutic compounds and its metabolites are present.

As used herein, the term "coadministering" refers to administration of the selected therapeutic agents (e.g., Quazepam and Bupropion) to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disorder or condition being treated. The result can be reduction and/or alleviation of the signs, symptoms, or causes of a disease, or any other desired alteration of a biological system. For example, an "effective amount" for therapeutic uses is the amount of the composition including a compound as described herein required to provide a clinically significant decrease in symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound described herein, such as Quazepam, is an amount effective to achieve a desired pharmacologic effect or therapeutic improvement without undue adverse side effects. It is to be understood that "an effective amount" or "a therapeutically effective amount" can vary from patient to patient, due to variation in metabolism of the compounds administered, the potency of the compounds used, the age, weight, and general condition of the patient, the condition being treated, the severity of the condition being treated, and the judgment of the prescribing physician.

A "serum concentration" or "plasma concentration" describes the blood serum or blood plasma concentration, typically measured in mg, μg, or ng of therapeutic agent per ml, dl, or l of blood serum, absorbed into the bloodstream after administration. As used herein, measurable plasma concentrations are typically measured in ng/ml or μg/ml.

The term "therapeutic window," as used herein, refers to a range of drug dosage (e.g., Bupropion dosage) which can treat the indicated condition effectively while avoiding more adverse effects than desired effects.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

DETAILED DESCRIPTION

Both insomnia and mood disorder conditions are debilitating health conditions that are widespread and can be extremely costly to society. Patients suffering from insomnia may also suffer from a mood disorder (e.g. depression). One of the common side effects of some antidepressants can be insomnia. In some cases patients suffering from insomnia or depression may require treatment with both a drug such as Quazepam (e.g., sold under the tradename Doral®) and a drug such as Bupropion (e.g., sold under the tradename Wellbutrin®). The safety and efficacy of such drug combinations, as described herein, is an important consideration for patients, the public and health care providers. For example, as described herein, patients treated with a sleep drug in combination a drug for another indication may be at risk for an adverse drug interaction including toxicity or reduced efficacy of one or both drugs.

The tricyclic benzodiazepine Quazepam (shown below), marketed as Doral®, is a sedative-hypnotic drug commonly used to treat insomnia.

Quazepam

Patients suffering from insomnia may also suffer from mood disorders (e.g., depression, bipolar disorder, and anxiety disorders), and vice versa. See, e.g., Ringdahl et al. (2004), *J. Am. Board Fam. Pract.*, 17:212-219. Further, a common side effect of the anti-depressant Bupropion is insomnia. Thus, patients suffering from both insomnia and a mood disorder (e.g., depression) may commonly be prescribed or treated with both a sedative-hypnotic drug (e.g., Quazepam) and an antidepressant (e.g., Bupropion). Indeed, as disclosed herein, Quazepam (shown below) is a mechanism-based inhibitor of the hydroxylase activity of P450 enzyme isoform 2B6 (CYP2B6), which is the primary enzyme responsible for clearance of the antidepressant drug Bupropion, as well as other drugs including, but not limited to, Efavirenz, Ifosfamide, RP73401 (piclamilast), testosterone, and S-mephobarbital. For convenience, a drug that is a substrate of the CYP2B6 enzyme is referred to hereinafter as a "CYP2B6 substrate drug."

Co-administration of Quazepam and a drug that is a substrate of the enzyme CYP2B6, e.g., a substrate that is hydroxylated by CYP2B6, such as Buproprion or Efavirenz, can increase the plasma concentration of the latter to an excessive level, e.g., a level outside of its therapeutic window. Increased plasma concentration of a CYP2B6 substrate drugs may have one or more adverse side effects on a patient, especially if they have a narrow therapeutic window. For example, elevated doses of Bupropion may precipitate seizures. See, e.g., Peck et al (1983), *J Clin Psychiatry*, 44(5 Pt 2):197-201. An excess level of Efavirenz (an anti-HIV drug) can cause adverse CNS events including, e.g., dizziness, insomnia, impaired concentration, drowsiness, or abnormal dreams.

Methods are described herein for reducing the risk of an adverse drug interaction in a patient identified as suffering from insomnia and in need of Quazepam. Such risk is reduced by assessing if a patient in need of Quazepam is being treated with a CYP2B6 substrate drug and providing a Quazepam treatment strategy based on the assessment.

In the methods described herein, a medical caregiver (e.g., a physician, psychiatrist, nurse, or pharmacist) can determine if a patient identified as suffering from insomnia is being treated with a CYP2B6 substrate drug (e.g., Bupropion or Efavirenz), and then can provide a treatment strategy to the patient based on this determination.

In some embodiments, a medical caregiver will prescribe or administer a therapeutically effective dose of Quazepam to a patient if, and only if, the patient is not being treated with a CYP2B6 substrate drug. Examples of CYP2B6 substrate drugs include, but are not limited to, Bupropion, Efavirenz, Ifosfamide, RP73401 (piclamilast), testosterone, and S-mephobarbital.

In other embodiments, if a patient identified as suffering from insomnia is not being treated with a CYP2B6 substrate drug for a second condition (e.g., depression), the medical caregiver prescribes or administers a therapeutically effective dose of Quazepam to treat the insomnia. However, if the patient is being treated with a CYP2B6 substrate drug, the patient is prescribed or administered a therapeutically effective dose of Quazepam, but is monitored for an adverse side effect while receiving treatment with both Quazepam and the CYP2B6 substrate drug. Alternatively, if the patient is being treated with CYP2B6 substrate drug to treat a second condition, treatment with the drug is discontinued, and the patient is then prescribed or administered Quazepam to treat the insomnia. In some embodiments, where treatment with the CYP2B6 substrate drug is stopped, an alternative drug that is not a CYP2B6 substrate is prescribed or administered to treat the second condition. In some embodiments, the second condition mention above is depression. In some embodiments, the second condition is nicotine addiction. In other embodiments, the second condition is an HIV infection or related condition.

In some embodiments, a medical caregiver determines if a patient identified as suffering from insomnia is being treated with a pharmacological composition containing Bupropion. If the patient is not being treated with a pharmacological composition containing Bupropion, the patient is prescribed or administered a therapeutically effective dose of Quazepam to treat the insomnia. However, if the patient is being treated with a pharmacological composition containing Bupropion, the patient is prescribed or administered a therapeutically effective dose of Quazepam, but is monitored for an adverse side effect while receiving treatment with both Quazepam and the CYP2B6 substrate drug. For example, the patient can be monitored in real time for onset of seizure activity using a device as described in, e.g., U.S. Pat. Nos. 6,658,287 and 5,311,876, the entire disclosures of which are incorporated by reference. In certain embodiments, when a patient is treated with both Quazepam and Bupropion, the plasma concentration of Bupropion can be regularly monitored to ensure that it does not exceed a threshold concentration, e.g., a plasma concentration outside of the therapeutic window for Bupropion, or a plasma concentration that does not induce side effects, or does not induce an unacceptable amount of side effects. In some embodiments, where the plasma concentration of Bupropion is found to be too high, a reduced dose of Quazepam, Bupropion, or both is prescribed or administered to the patient. Alternatively, treatment with Bupropion is discontinued.

In some embodiments, where a patient is being treated with a CYP2B6 substrate drug, the patient is genotyped for one or more polymorphisms associated with reduced CYP2B6 expression or activity, such general procedures as described in, e.g., Lang et al (2004), *J Pharmacol*, 311(1):34-43; and Lamba et al (2003), *J of Pharmacol and Exp Therapeutics*, 307:906-922. Where the patient is found to be positive for a polymorphism associated with reduced CYB2B6 expression or activity, a reduced dose of the CYP2B6 substrate drug (e.g., Bupropion or Efavirenz) is or can be prescribed or administered prior to treating the patient with Quazepam. Alternatively, if the patient is positive for a polymorphism associated with reduced CYB2B6 expression or activity, treatment with the CYP2B6 substrate drug is discontinued prior to prescribing or administering Quazepam to the patient.

In some embodiments, if a patient suffering from insomnia is identified as being treated with a pharmacological composition containing Bupropion, treatment with the Bupropion is stopped, and the patient is then prescribed or administered Quazepam to treat the insomnia. In some embodiments, where treatment with the pharmacological composition containing Bupropion is stopped, an alternative drug to Bupropion is prescribed or administered to the patient. For example, where Bupropion is used to treat depression, suitable alternative antidepressant drugs include but not limited to, fluvoxamine (Luvox®), paroxetine (Paxil®), fluoxetine (Prozac®), or sertraline (Zoloft®), amitriptyline (Elavil®, Endep® Tryptanol®), clomipramine (Anafranil®), desipramine (Norpramin®, Pertofrane®), dothiepin hydrochloride (Prothiaden®, Thaden®), doxepin (Adapin®, Sinequan®), imipramine (Tofranil®), lofepramine (Gamanil®, Lomont®), nortriptyline (Pamelor®), protriptyline (Vivactil®), and trimipramine (Surmontil®), isocarboxazid (Marplan®), moclobemide (Aurorix®, Manerix®, Moclodura®), phenelzine (Nardil®), tranylcypromine (Parnate®), selegiline (Eldepryl®), nialamide, iproniazid (Marsilid,® Iprozid®, Ipronid®, Rivivol®, Propilniazida®), iproclozide, and toloxatone.

In some embodiments, the alternative antidepressant is a substrate of the CYP2B6 enzyme, e.g., fluvoxamine, paroxetine, fluoxetine, sertraline, or selegiline.

In other embodiments, the alternative antidepressant is a drug that is not a substrate of the CYP2B6 enzyme. Such antidepressant drugs include, but are not limited to amitriptyline (Elavil®, Endep® Tryptanol®), clomipramine (Anafranil®), desipramine (Norpramin®, Pertofrane®), dothiepin hydrochloride (Prothiaden®, Thaden®), doxepin (Adapin®, Sinequan®), imipramine (Tofranil®), lofepramine (Gamanil®, Lomont®), nortriptyline (Pamelor®), protriptyline (Vivactil®), and trimipramine (Surmontil®), isocarboxazid (Marplan®), moclobemide (Aurorix®, Manerix®, Moclodura®), phenelzine (Nardil®), tranylcypromine (Parnate®), nialamide, iproniazid (Marsilid,® Iprozid®, Ipronid®, Rivivol®, Propilniazida®), iproclozide, and toloxatone.

In some embodiments, the alternative antidepressant is a selective serotonin reuptake inhibitor (SSRI), including, but not limited to, citalopram (Celexa, Cipramil, Emocal, Sepram, Seropram), escitalopram (Lexapro, Cipralex, Esertia), fluoxetine, fluvoxamine, paroxetine, sertraline, or orzimelidine (Zelmid, Normud).

Where Bupropion is used to treat nicotine addiction suitable alternative drugs that are not CYP2B6 substrate drugs include, but are not limited to, Varenicline (Chantix®), Clonidine (Clopres), and Nortryptiline (Pamelor®).

In some embodiments, a patient suffering from insomnia is being treated for a second condition with Bupropion. In other embodiments, a patient suffering from insomnia is being treated for a second condition with Efavirenz.

In some embodiments, a patient suffering from insomnia also suffers from a second condition that can be treated with a CYP2B6 substrate drug. Examples of such conditions include, but are not limited to, depression (treated with, e.g., Bupropion), nicotine addiction (treated with, e.g., Bupropion), HIV infection (treated with, e.g., Efavirenz), anxiety, epilepsy (treated with, e.g., S-mephobarbital), cancer (treated with, e.g., Ifosfamide). In some embodiments, a patient suffering from insomnia also suffers from depression. In other embodiments, a patient suffering from insomnia also has an HIV infection.

In some embodiments, the risk of an adverse drug interaction in a patient being treated with Quazepam is reduced by determining if the patient is in need of treatment for depression, and if so, prescribing or administering a therapeutically effective amount of a drug (e.g., an antidepressant drug) other than Bupropion to the patient. In some cases, antidepressant drugs other than Bupropion include those that are not substrates of the CYP2B6 enzyme. In other cases, antidepressant drugs other than Bupropion include antidepressant drugs that are substrate of the CYP2B6 enzyme. In some embodiments, where an antidepressant drug has a narrow therapeutic range, the antidepressant drug is suitable for use if it is not a substrate of the CYP2B6 enzyme. In other embodiments, where an antidepressant drug has a wide therapeutic range, the antidepressant drug is a CYP2B6 substrate.

A medical caregiver can determine if a patient is being treated with a CYP2B6 substrate drug by inquiring with the patient, reviewing the patient's medical history file, inquiring with another medical caregiver who is treating the same patient, or by other methods known or easily determined by one of skill in the art. For example, the medical caregiver can determine if the patient is being treated with any one or more of the following exemplary CYP2B6 substrate drugs: Bupropion (Wellbutrin®, Zyban®), Efavirenz (Sustiva®, Stocrin®), Ifosfamide (Mitoxana®), S-mephobarbital (Mebaral).

The plasma levels of any one or more of these drugs, or a metabolite thereof can be determined in a biological sample from the patient (e.g., serum, plasma, or urine) by a number of analytical tests known in the art, e.g., liquid chromatography-mass spectrometry (LC-MS) or liquid chromatography with fluorescence detection (LC-FLD), or high performance liquid chromatography. See, e.g., Kovacevic et al. (2006), *J. Chromatogr. Analyt. Technol. Biomed. Life Sci.,* 830(2):372-376; and Hemke et al. (2000), *Pharmacol. Ther.,* 85(1): 11-28; Segura et al. (2001), *J. Anal. Toxicol.* 25(2): 130-136.

Criteria for the diagnosis of psychiatric disorders, and the prescription, administration, and dosing of hypnotic benzodiazepines and antidepressants are described in, e.g., the "Diagnostic and Statistical Manual of Mental Disorders©," 4th ed., 1994, American Psychiatric Association; and Walsh (2004), *J Clin Psychiatry,* 65 Suppl. 16:41-45; and Edwards et al. (1999), *Drugs,* 57(4):507-533.

For any given patient, a therapeutically effective amount of Quazepam or Bupropion (or any other CYP2B6 substrate drug) will depend on the severity and course of the condition(s), concurrent treatment with a CYP2B6 substrate drug, presence of polymorphisms associated with reduced CYP2B6 expression or activity, the patient's health status, age, weight, and response to the drugs, the judgment of the treating medical caregiver and/or the approved dosage and guidelines approved by the U.S. FDA or other US or foreign regulatory authority. Typically, a therapeutically effective amount of Quazepam ranges from about 2 mg/day to about 20 mg/day, e.g., 4 mg/day, 5 mg/day, 7 mg/day, 10 mg/day, 12 mg/day, 15 mg/day, 18 mg/day or any other dose from about 2 mg/day to about 20 mg/day, administered orally. Typically, a therapeutically effective amount of Bupropion ranges from a total dose of about 50 mg/day to about 450 mg/day, e.g., 50 mg/day, 70 mg/day, 100 mg/day, 120 mg/day, 150 mg/day, 180 mg/day, 200 mg/day, 220 mg/day, 250 mg/day, 300 mg/day, 350 mg/day, 400 mg/day, or any other dose from about 50 mg/day to about 450 mg/day. However, no single dose of Bupropion should exceed 150 mg.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Reference thereto evidences the availability and public dissemination of such information.

Example 1

Time, Concentration, and NADPH-Dependent Inhibition of the CYP450 2B6 Isoform (CYP2B6) by Quazepam We sought to determine if Quazepam could inhibit the catalytic activity of the cytochrome P450 enzyme isoform 2B6 (GenBank Accession No. NM_000767; EC number 1.14.14.1) which is the primary metabolizing enzyme for a number of widely prescribed pharmaceutical compounds, e.g., Bupropion, Efavirenz, and Ifosfamide.

The ability of Quazepam to inhibit CYP2B6 activity was measured in pooled human liver microsomes. The assay conditions are described in Table 1:

TABLE 1

| | CYP2B6 Inhibition Assay Conditions | | | | | |
|---|---|---|---|---|---|---|
| Marker Substrate | Substrate Conc. (µM) | Incubation Time (min) | Protein Conc. (mg/ml) | Metabolite | Positive Control Inhibitor | Inhibitor Concentration (µM) |
| Bupropion | 125 | 20 | 0.25 | HydroxyBupropion | ThioTEPA | 75 |

Microsomal incubations to monitor CYP2B6 activity were performed in duplicate with Quazepam concentrations of 0, 0.5, 1.5, 5, 15, and 50 µM. The total amount of organic solvent was <1%. Each incubation included 0.1 M phosphate buffer (pH 7.4), substrate, inhibitor and microsomal protein in a final volume of approximately 0.5 mL. Reactions were initiated by addition of NADPH (1 mM final concentration) and incubated for the indicated times at 37° C. with gentle agitation.

Additionally, time-dependent inhibition of CYP2B6 activity by Quazepam was measured in pooled human liver microsomes. Identical incubation conditions were used as with the direct inhibition analysis (see Table 1) with the exception that microsomes were pre-incubated for 30 minutes with Quazepam (0, 0.5, 1.5, 5, 15, and 50 µM) and the P450 enzyme cofactor NADPH (1 mM). Following the 30 minute pre-incubation period, substrate and additional NADPH (1 mM) were added to all samples and incubated for the indicated times at 37° C. with gentle agitation. All microsomal incubations were performed in duplicate.

Control incubations included positive inhibitor control samples for direct inhibition as well as samples without NADPH. All reactions were terminated by the addition of organic solvent, and internal standard was added (when appropriate), and samples were mixed and centrifuged at approximately 3000 rpm for 10 minutes. The organic layer was transferred to a clean tube and evaporated to dryness at about 40° C. under nitrogen. The sample was reconstituted and analyzed by LC MS/MS.

In addition to metabolite standard curves and bioanalytical metabolite quality control samples (QC), quality control incubations ($QC_i$) were included in each experimental run. These samples ensured that the enzyme system was performing in a consistent manner as compared to the original method validation. These samples consisted of at least five different concentration levels of a CYP450 isoform marker substrate. The rates of metabolite formation from these samples were plotted against total substrate concentration and a $K_m$ value determined (data not shown). For the experimental day to pass, this value was considered to be within the acceptance criteria determined during validation. Additional controls included samples for ionization suppression assessment and test compound specificity.

To determine the kinetic parameters ($K_I$ and $k_{inact}$) for the time-dependent inactivation of CYP2B6 by Quazepam, a detailed time- and concentration-dependence experiment was performed. Time-dependent inactivation of CYP2B6 by Quazepam in human liver microsomes was tested by independently following decreases in CYP2B6-catalyzed Bupropion hydroxylation over time. Duplicate samples containing approximately 2.5 mg/mL protein were pre-incubated for various time intervals (0, 3, 5, 10, 20, and 30 minutes) at 37° C. with several concentrations of Quazepam (0, 0.2, 0.5, 2, 5 and 20 µM) in the presence of 1 mM NADPH. After the pre-incubation period, the primary incubations were diluted 10 fold into a secondary incubation containing marker substrate (625 µM Bupropion) and additional NADPH (1 mM). The secondary incubation reactions were stopped after 20 minutes by the addition of isoamyl alcohol and ethyl acetate (1:100, v:v), and hydroxyBupropion concentrations were determined using a validated LC-MS/MS method (see Analytical Methods Section below). As a control to demonstrate NADPH-dependence for time-dependent inhibition, 20 µM Quazepam was pre-incubated for 0, 3, 5, 10, 20, and 30 minutes without NADPH. Additionally, positive control samples containing 10 µM ticlopidine (positive control), a known time dependent inhibitor of CYP2B6, were pre-incubated in duplicate for the time intervals indicated above.

Analytical Methods

Mass spectrometric data was acquired, integrated, regressed, and quantified with MassLynx software, version 3.4 (Micromass, Manchester, United Kingdom).

Method for Analysis of CYP2B6 Activity

Incubations to determine CYP2B6-mediated conversion of Bupropion to hydroxyBupropion (OHBP) in microsomal preparations were terminated by addition of 2.5 mL isoamyl alcohol: ethyl acetate (1:100, v:v). The internal standard, hydroxyBupropion-$d_6$, and a saturated sodium chloride solution (0.25 mL) were added to all samples. The organic layer was transferred to a new tube, evaporated to dryness and reconstituted in 40% methanol, 60% 1 mM ammonium acetate buffer, 0.1% formic acid. OHBP formation was measured using an LC-MS/MS method and the analytical parameters listed in Table 2.

Mass spectrometric data was acquired, integrated, regressed, and quantified with MassLynx software, version 3.4 (Micromass, Manchester, United Kingdom).

TABLE 2

LC-MS/MS Analytical Parameters for 2B6 Bupropion Hydroxylation Assay
CYP2B6

| | |
|---|---|
| Substrate:Metabolite: | Bupropion:OHBP |
| Standard Metabolite Range: | 1.00 to 1000 ng/mL |
| Internal Standard: | Hydroxybupropion-$d_6$ |
| Mobile Phase (isocratic): | 40% Methanol, 60% 1 mM Ammonium Acetate Buffer, 0.1% Formic Acid |
| Detection Method: | LC-MS/MS |
| HPLC Column: | YMC-ODS-AQ, 3 µm, 4.0 × 50 mm, Waters |
| Flow rate (approx.): | 0.4 mL/min |
| Source: | Electrospray (positive ion) |
| Run Time (approx.): | 4.2 minutes |
| MRM (OHBP): | 256 → 238 |
| MRM (internal std): | 262 → 244 |
| Quantitation: | Least Squares Regression 1/$X^2$ Weighting |

Data Analyses

Data Analysis for IC50 Determination

Data were graphed with the software program Microsoft Excel® (Redmond, Wash.). Reaction velocities (V) were calculated using Equation 1:

$V$(nmol/min/mg)=calculated ng/mL×0.5 mL/($MW$ ng/nmol)/min/mg            Equation 1

Percentage of remaining activity was determined using the following equation:

% Remaining Activity=($V_{sample/mean}$ of $V$control×100)            Equation 2

If ≧50% inhibition was observed, IC50 values were determined by linear regression.

Statistical analyses included determining descriptive statistics such as mean, standard deviation, relative standard deviation, and linear regression analyses, where appropriate.

Data Analysis for Ki Determination

Data were graphed with the software program Microsoft Excel® (Redmond, Wash.). Reaction velocities (V) were calculated using Equation 1 from above.

The most appropriate inhibition model (competitive, non-competitive, linear-mixed or uncompetitive) was determined using a combination of both graphical and statistical methods. Specifically, a Lineweaver-Burke plot was used to assess the mechanism of inhibition in conjunction with a comparison of statistical parameters from the nonlinear regression analysis using Systat® 6.0.1 (SPSS, Inc., Chicago, Ill.). These parameters typically consist of: residual sum of squares, examination of the asymptotic standard error for each of the parameters and the R-squared value. Based on this assessment, the most appropriate inhibition model for the estimation of a $K_i$ value was selected (see Table 3). The following standard equations were used to determine the $K_i$ value for each model where V is the rate of metabolism, $V_{max}$ is the maximum rate of metabolism, $K_m$ is the Michaelis constant, $K_i$ is the inhibitor constant, [I] is the inhibitor concentration [S] is the substrate concentration and A is the factor by which the $K_i$ changes in the presence of substrate (see, e.g., Bjornsson et al (2003), *Drug Metab. Dispos.*, 31:815-832).

TABLE 3

P450 Enzyme Inhibition Models

| Model Type | Equation |
|---|---|
| Competitive | $V = V_{max}*[S]/((K_m*(1 + ([I]/K_i))) + [S])$ |
| Noncompetitive | $V = V_{max}*[S]/((K_m*(1 + ([I]/K_i))) + [S]*(1 + ([I]/K_i)))$ |
| Linear-mixed | $V = V_{max}*[S]/((K_m*(1 + ([I]/K_i))) + [S]*(1 + ([I]/A*K_i)))$ |
| Uncompetitive | $V = V_{max}*[S]/((K_m + [S]*(1 + ([I]/K_i)))$ |

Data Analysis for Time-Dependent Inhibition Kinetic Parameters

Data were graphed with the software program Microsoft Excel® (Redmond, Wash.). All experiments were monitored relative to a control sample without Quazepam. The enzyme activity in this sample was set to 100% at each time point (Silverman et al (1995), *Methods Enzymol*, 249:240-283), taking into account the background loss of enzyme activity under reaction conditions. The percent remaining activity after incubation for each pre-incubation time point at each Quazepam concentration was plotted as the natural log(ln) of the mean % of control activity vs. primary incubation time. The initial rate constant for enzyme inactivation (kobs or kapp) at each concentration of Quazepam was estimated from the plot, where the slope of a linear regression line is $-k_{app}$. The $k_{inact}$ (the maximum rate constant for inactivation) and $K_I$ (the inactivator concentration at half the maximal rate of enzyme inactivation) values were determined from linear regression of a double-reciprocal (Kitz Wilson) plot of the $k_{app}$ values versus the Quazepam concentrations where $k_{inact}$ is equal to 1/y-intercept and $K_I$ is equivalent to –1/x-intercept.

Results

Figure 1:
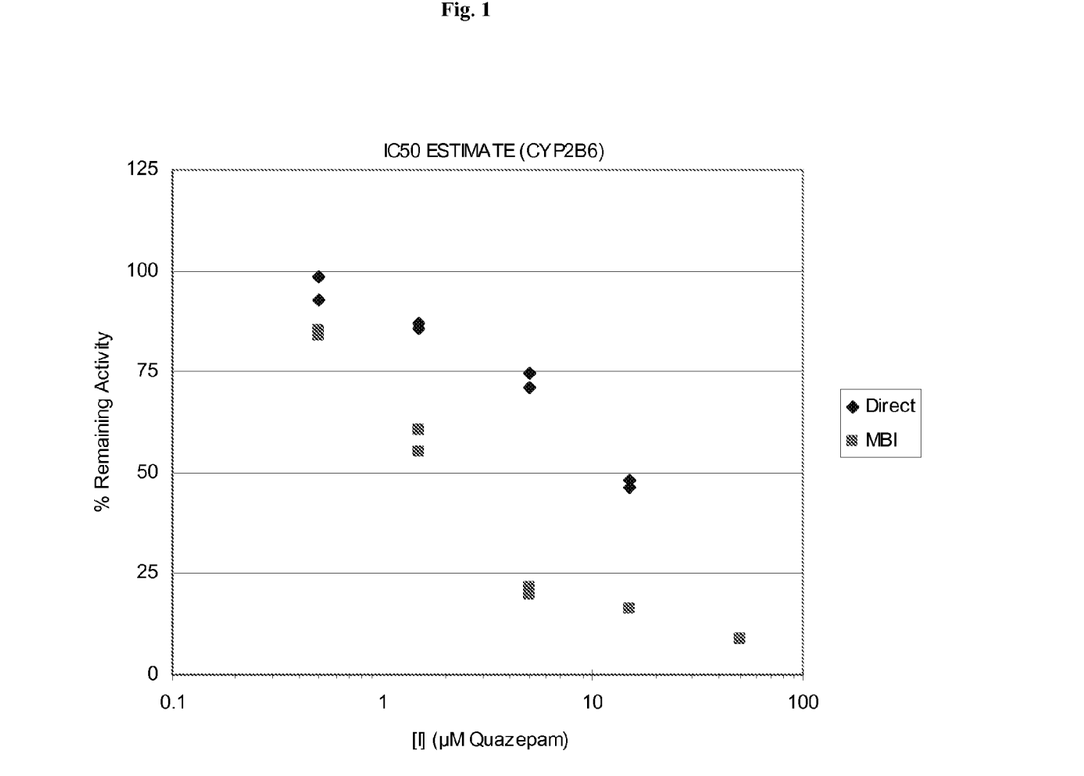
FIG. 1 is a scatter plot showing Quazepam concentration versus CYP2B6 (Bupropion Hydroxylase) activity in vitro, which is used to determine the Quazepam $IC_{50}$ for direct and time-dependent (mechanism-based) inhibition of CYP2B6.

Inhibitory effects of Quazepam on activities of CYP2B6 in human microsomes were measured. A summary of the direct and time-dependent (MBI) inhibitory activity by Quazepam is presented in Tables 4 and 5, respectively. The estimated IC50 values for direct and time-dependent mechanism-based inhibition are shown in Table 6. See also FIG. 1.

TABLE 4

Direct Inhibition of 2B6 by Quazepam

| Quazepam (μM) | Mean % Remaining Activity 2B6 |
|---|---|
| 0 | 100 |
| 0.5 | 95.7 |
| 1.5 | 86.5 |
| 5 | 72.9 |
| 15 | 47.1 |
| 50 | 109 |
| Positive Control | 22.8 |

TABLE 5

Time-Dependent (Mechanism Based) Inhibition of 2B6 by Quazepam

| Quazepam (μM) | Mean % Remaining Activity 2B6 |
|---|---|
| 0 | 100 |
| 0.5 | 84.7 |
| 1.5 | 57.9 |
| 5 | 20.7 |
| 15 | 16.4 |
| 50 | 8.9 |

TABLE 6

| | Estimated IC$_{50}$ (μM) | |
|---|---|---|
| P450 Isoform | Direct Inhibition | Time-dependent (MBI) Inhibition |
| CYP2B6 | 13.9 | 2.2 |

Pre-incubation of Quazepam at concentrations up to 50 μM with CYP2B6, in the presence of NADPH resulted in a decrease of ~6-fold in the IC50 values of CYP2B6 (IC50=2.2 μM), suggesting that Quazepam is a possible time dependent (mechanism-based) inhibitor of CYP2B6 (Table 6). The kinetic parameters ($k_{inact}$ and $K_I$) for time-dependent inhibition were determined for CYP2B6 (as measured by Bupropion hydroxylation) (Table 7 and FIGS. 2-3).

The inhibition of CYP2B6 was found to be time- and concentration-dependent with $k_{inact}$ and $K_I$ values of 0.0170 min$^{-1}$ and 3.0 μM, respectively.

Figure 2:
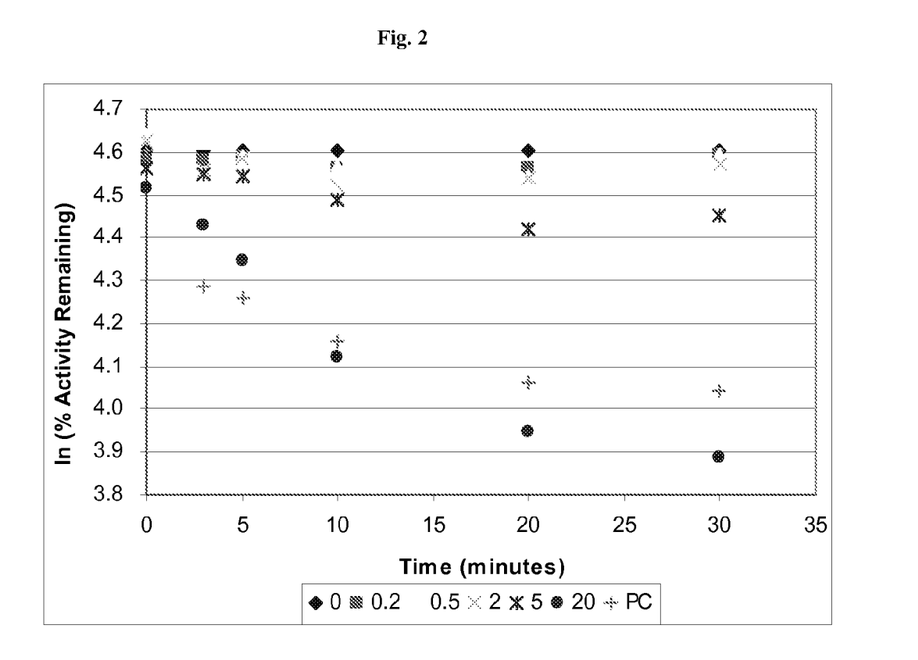
FIG. 2 is a scatter plot showing time-dependent inhibition of CYP2B6-catalyzed Bupropion hydroxylation by Quazepam in human liver microsomes.
Figure 3:
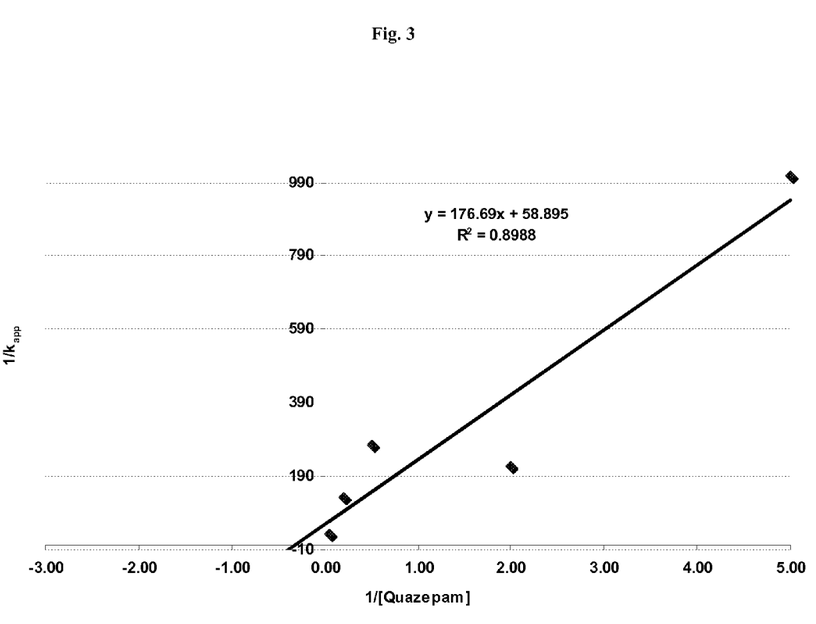
FIG. 3 is a Kitz-Wilson (Double Reciprocal) plot used to determine the kinetic parameters of time-dependent inactivation of CYP2B6 by Quazepam.

Ticlopidine, a known mechanism-based inhibitor of CYP2B6 was included as a positive control (PC). Ticlopidine, a known mechanism-based inhibitor of CYP2B6 showed time-dependent inhibition (Table 7; FIG. 2) demonstrating suitable reaction conditions. The inhibition of CYP2B6 was also found to be NADPH-dependent.

Figure 4:
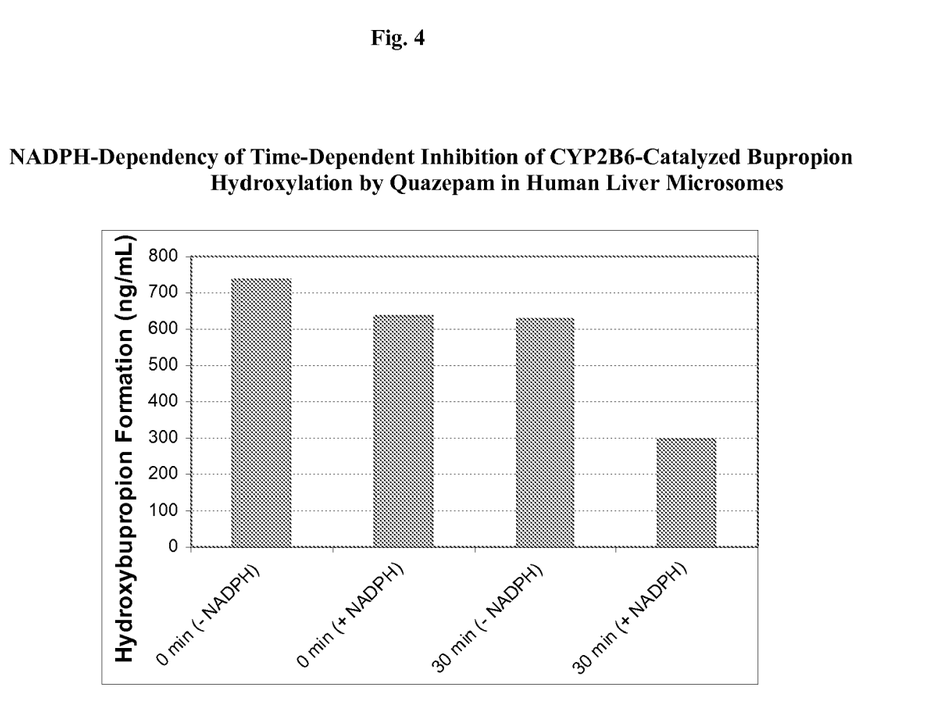
FIG. 4 is a bar graph illustrating the NADPH-Dependency of time-dependent Inhibition of CYP2B6-Catalyzed Bupropion Hydroxylation by Quazepam in human liver microsomes.

Control samples pre incubated for 30 minutes with 20 μM Quazepam in the presence of NADPH showed increased inhibition as compared to samples without NADPH (52.9% increase in inhibition in the presence of NADPH) suggesting that the time-dependent inhibition is, at least in part, metabolism based (Table 8; FIG. 4).

TABLE 7

Data for CYP2B6 Time-Dependent Kinetic Parameter Determination

| Inhibitor Conc. (uM) | Time (minutes) | Status | Average Activity (ng/mL)[+] | % Activity Relative to time | ln mean % to control | Slope | R$^2$ |
|---|---|---|---|---|---|---|---|
| 0 | 0 | | 699 | 100 | 4.61 | 9.51E−33 | |
| | 3 | | 666 | 100 | 4.61 | | |
| | 5 | | 668 | 100 | 4.61 | | |
| | 10 | | 676 | 100 | 4.61 | | |

TABLE 7-continued

Data for CYP2B6 Time-Dependent Kinetic Parameter Determination

| Inhibitor Conc. (uM) | Time (minutes) | Status | Average Activity (ng/mL)[+] | % Activity Relative to time | ln mean % to control | Slope | $R^2$ |
|---|---|---|---|---|---|---|---|
|  | 20 |  | 647 | 100 | 4.61 |  |  |
|  | 30 |  | 605 | 100 | 4.61 |  |  |
| 0.2 | 0 |  | 682 | 97.6 | 4.58 | −9.94E−04 | 0.72 |
|  | 3 |  | 649 | 97.5 | 4.58 |  |  |
|  | 5 | * | 658 | 98.5 | 4.59 |  |  |
|  | 10 |  | 647 | 95.7 | 4.56 |  |  |
|  | 20 |  | 620 | 95.9 | 4.56 |  |  |
|  | 30 | * | 599 | 99.0 | 4.60 |  |  |
| 0.5 | 0 |  | 724 | 104 | 4.64 | −4.60E−03 | 0.88 |
|  | 3 |  | 677 | 102 | 4.62 |  |  |
|  | 5 |  | 657 | 98.4 | 4.59 |  |  |
|  | 10 |  | 652 | 96.4 | 4.57 |  |  |
|  | 20 |  | 609 | 94.2 | 4.55 |  |  |
|  | 30 | * | 599 | 99.0 | 4.59 |  |  |
| 2 | 0 |  | 714 | 102 | 4.63 | −3.64E−03 | 0.50 |
|  | 3 |  | 636 | 95.5 | 4.56 |  |  |
|  | 5 | * | 654 | 97.9 | 4.58 |  |  |
|  | 10 |  | 622 | 92.0 | 4.52 |  |  |
|  | 20 |  | 605 | 93.5 | 4.54 |  |  |
|  | 30 | * | 583 | 96.5 | 4.57 |  |  |
| 5 | 0 |  | 671 | 95.9 | 4.56 | −7.61E−03 | 0.98 |
|  | 3 |  | 630 | 94.6 | 4.55 |  |  |
|  | 5 |  | 629 | 94.2 | 4.55 |  |  |
|  | 10 |  | 601 | 88.9 | 4.49 |  |  |
|  | 20 |  | 537 | 83.0 | 4.42 |  |  |
|  | 30 | * | 518 | 85.7 | 4.45 |  |  |
| 20 | 0 |  | 638 | 91.3 | 4.51 | −2.92E−02 | 0.96 |
|  | 3 |  | 558 | 83.8 | 4.43 |  |  |
|  | 5 |  | 516 | 77.3 | 4.35 |  |  |
|  | 10 |  | 418 | 61.8 | 4.12 |  |  |
|  | 20 |  | 334 | 51.7 | 3.95 |  |  |
|  | 30 | * | 295 | 48.8 | 3.89 |  |  |
| PC | 0 |  | 120 | 100 | 4.61 | −1.47E−02 | 0.67 |
|  | 3 |  | 87.2 | 72.8 | 4.29 |  |  |
|  | 5 |  | 84.7 | 70.7 | 4.26 |  |  |
|  | 10 |  | 76.7 | 64.0 | 4.16 |  |  |
|  | 20 |  | 69.5 | 58.1 | 4.06 |  |  |
|  | 30 |  | 68.4 | 57.1 | 4.05 |  |  |

[+]Refers to metabolite formation.
* Data not included in slope calculations; Not linear with time.

TABLE 8

NADPH Dependency of CYP2B6 Time-Dependent Inhibition by Quazepam

| ID | Inhibitor Conc. (µM) | Pre-incubation Time (min) | Average Activity (ng/mL) | % Remaining Activity |
|---|---|---|---|---|
| 0 min (−NADPH) | 20 | 0 | 737 | 86.6 |
| 0 min (+NADPH) |  |  | 638 |  |
| 30 min (−NADPH) |  | 30 | 626 | 47.1 |
| 30 min (+NADPH) |  |  | 295 |  |

For example, and based at least in part on these data, we concluded that Quazepam is a mechanism based inhibitor of the CYP2B6 enzyme.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for reducing the risk of an adverse drug interaction in a patient suffering from depression, comprising
   (i) determining if the patient is also suffering from insomnia and is being treated with bupropion, and
   (ii) prescribing or administering to the patient a therapeutically effective amount of quazepam to treat the insomnia if and only if the patient is not being treated with bupropion.

2. The method of claim 1, wherein the patient is not being treated with bupropion, further comprising prescribing or administering to the patient an antidepressant drug other than bupropion.

* * * * *